(12) United States Patent
Saller et al.

(10) Patent No.: US 6,776,985 B1
(45) Date of Patent: Aug. 17, 2004

(54) ENCAPSULATED CELLS PRODUCING VIRAL PARTICLES

(75) Inventors: Robert Michael Saller, München (DE); Walter H. Günzburg, Mölding (AT); Brian Salmons, Ainhofen (DE)

(73) Assignees: Bavarian Nordic A/S, Copenhagen (DK); GSF-Gesellschaft fur Umwelt und Gesundheit GmbH, Neuherberg (DE)

( * ) Notice: Subject to any disclaimer, the term of this patent is extended or adjusted under 35 U.S.C. 154(b) by 286 days.

(21) Appl. No.: 08/996,460

(22) Filed: Dec. 23, 1997

Related U.S. Application Data

(63) Continuation of application No. PCT/EP96/02748, filed on Jun. 27, 1995.

(30) Foreign Application Priority Data

Jun. 27, 1995 (DK) ............................................. 0740/95

(51) Int. Cl.$^7$ .......................... A01N 63/00; A01N 9/62; A01N 43/04; C10N 15/63
(52) U.S. Cl. ................ 424/93.21; 435/69.1; 435/320.1; 435/325; 435/455; 424/93.1; 424/93.2; 424/451; 424/461; 514/44
(58) Field of Search ............................ 435/69.1, 320.1, 435/325, 455; 424/93.1, 93.21, 93.2, 451, 461; 514/44, 69.1

(56) References Cited

U.S. PATENT DOCUMENTS

| | | | |
|---|---|---|---|
| 4,391,909 A | 7/1983 | Lim | ........................... 435/178 |
| 5,328,470 A | * 7/1994 | Nabel et al. | ................. 604/101 |

FOREIGN PATENT DOCUMENTS

| | | | | |
|---|---|---|---|---|
| DE | 4021050 A1 | 1/1992 | | |
| EP | 199362 A2 | 10/1986 | | |
| EP | 243204 A2 | 10/1987 | | |
| EP | 476953 A2 | 3/1992 | | |
| GB | 2135954 A | 9/1984 | | |
| GB | 2 135 954 A | * 9/1984 | ............ | B01J/13/02 |
| GB | 2159172 A | 11/1985 | | |
| GB | 2 159 172 A | * 11/1985 | ............ | C12N/5/00 |
| WO | WO 89/11539 | 11/1989 | | |
| WO | WO92/10564 | 6/1992 | | |
| WO | WO 94/29437 | 12/1994 | | |
| WO | WO 96/04789 | 2/1996 | | |
| WO | WO 96/07748 | 3/1996 | | |
| WO | WO 97/01357 | 1/1997 | | |
| WO | WO 97/09440 | 3/1997 | | |
| WO | WO 97/35994 | 10/1997 | | |

OTHER PUBLICATIONS

Walther et al., Viral vectors for gene transfer,2000,Drugs, vol. 60 (2), pp. 249–271.*
Varmus, Gene therapy: Not ready for prime time, 1996, Nature Medicine, vol. 2 (1), pp. 7–8.*
Verma et al., Gene therapy—promises, problems and prospects, 1997, Nature, vol. 389, pp. 239–242.*
Anderson, Human gene therapy, 1998,Nature, vol. 392, pp. 25–30.*
Friedmann, Principles for human gene therapy studies, 2000, Science, vol. 287, pp. 2163–2164.*
Rosenberg et al., Gene therapist, heal thyself, 2000, Science, vol. 287, p. 1751.*
Verma, Gene therapy: Beyond 2000, 2000, Molecular Therapy, p. 493.*
Ali et al., The use of DNA viruses as vectors for gene therapy, 1994, Gene Therapy, vol. 1, pp. 367–384.*
Friedmann, Gene Therapy 1:217–218, 1994.*
Miller, PNAS 93:11407–13, 1996.*
Lewis et al, J. Virol. 68(1):510–516, 1994.*
Sandrin et al, PNAS, 90:11391–11395 1993.*
Stange et al, Biomat. Art. Cells & Immob. Biotech. 21(3), 343–352, 1993.*
Kotani et al, Hum Gene .Ther. 5:19–28, 1994.*
Vile et al, Gene Therapy 1:88–98, 1994.*
Wie, M.X., "Experimental Tumor Therapy in Mice Using the Cyclophosphamide–Activating Cytochrome P450 2B1 Gene," *Human Gene Therapy* 5:969–978 (Aug. 1994).
Wright, J.E., et al., "Analysis of 4–Hydroxycyclophosphamide in Human Blood," *Analy. Biochem.*, 224(1):154–158 (1995).
Connors, T.A., "The choice of prodrugs for gene directed enzyme prodrug therapy of cancer," *Gene Ther.*, 2(10):702–709 (1995).
Salmons, B., et al., "Construction of Retroviral Vectors for Targeted Delivery and Expression of Therapeutic Genes," *Leukemia,* 9(Supplement 1): S53–S60 (1995).
Chen, S.H., et al., "Gene therapy for brain tumors: Regression of experimental gliomas by adenovirus–mediated gene transfer in vivo," *Proc. Natl. Acad. Sci. USA,* 91(8):3054–3057 (1994).
Donato, M.T., et al., "A Microassay for Measuring Cytochrome P450IA1 and P450IIB1 Activities in Intact Human and Rat Hepatocytes Cultured on 96–Well Plates", *Analyt. Biochem.,* 213(1):29–33 (1993).
Freeman, S.M., et al., "The Bystander Effect": Tumor Regression When a Fraction of the Tumor Mass is Genetically Modified, *Can. Res.,* 53(21):5274–5283 (1993).
Vile, R. G. and Hart, I. R., "Use of Tissue–specific Expression of the Herpes Simplex Virus Thymidine Kinase Gene to Inhibit Growth of Established Murine Melanomas following Direct Intratumoral Injection of DNA", *Can. Res.,* 53(17):3860–3864 (1993).

(List continued on next page.)

*Primary Examiner*—Jeffrey Fredman
(74) *Attorney, Agent, or Firm*—Hamilton, Brook, Smith & Reynolds, P.C.

(57) ABSTRACT

The present invention relates to encapsulated cells producing viral particles, especially retroviral particles containing the genome of a retroviral vector carrying therapeutic genes, to methods for the preparation of such encapsulated cells, as well as to the use of such encapsulated cells for the delivery of genes, especially therapeutic genes, to target organs/cells.

28 Claims, 3 Drawing Sheets

OTHER PUBLICATIONS

Bi, W. L., et al., "In Vitro Evidence That Metabolic Cooperation Is Responsible for the Bystander Effect Observed with HSV tk Retroviral Gene Therapy", *Human Gene Ther.,* 4(6):725–731 (1993).

Tiano, H. F., et al., "Retroviral mediated expression of human cytochrome P450 2A6 in C3H/10T1/2 cells confers transformability by 4–(methylnitrosamino)–1–(3–pyridyl)–1–butanone (NNK)", *Carcinog.,* 14(7):1421–1427 (1993).

Salmons, B. and Günzburg, W. H., "Targeting of Retroviral Vectors For Gene Therapy", *Human Gene Ther.,* 4(2):129–141 (1993).

Kolb, A.F., "Characterization of a Protein that Binds a negative Regulatory Element in the Mammary–Specific Whey Acidic Protein Promoter", *Biochem. Biophys. Res. Comm.,* 217(3):1045–1052 (1995).

Salmons, B., et al., "Production of Mouse Mammary Tumor Virus upon Transfection of a Recombinant Proviral DNA into Cultured Cells", *Virol.,* 144:101–114 (1985).

Fujii–Kuriyama, Y., et al., "Primary structure of a cytochrome P–450: Coding nucleotide sequence of phenobarbital–inducible cytochrome P–450 cDNA from rat liver", *Proc. Natl. Acad. Sci. USA,* 79:2793–2797 (1982).

Kedzie, K. M., et al., "Molecular Basis for a Functionally Unique Cytochrome P450IIB1 Variant", *J. Biol. Chem.,* 266(33):22515–22521 (1991).

Connors, T. A., "Prodrugs in cancer chemotherapy", *Xenobiot.,* 16(10/11):975–988 (1986).

Connors, T. A. and Whisson, M. E., "Cure of Mice bearing Advanced Plasma Cell Tumours with Aniline Mustard: the Relationship between Glucuronidase Activity and Tumor Sensitivity", *Nature,* 210:866–867 (1966).

Kay, M.A., et al., "Gene therapy," *Proc. Natl. Acad. Sci, USA,* 94:12744–12746 (1997).

Kelloff, G.J., et al., "Cancer Chemoprevention: Progress and Promise," *European Journal of Cancer,* 35(14):2031–2038 (1999).

Gömez–Navarro, J., et al., "Gene Therapy for Cancer," *European Journal of Cancer,* 35(6):867–885 (1999).

Mastrangelo, M.J., et al., "Gene Therapy for Human Cancer: An Essay for Clinicians," *Seminars in Oncology,* 23(1):4–21 (1996).

Fabre, J.W., "Nudging xenotransplantation towards humans," *Nature Medicine,* 1(5):403–404 (1995).

Abbas, A.K., "Die and Let Live: Eliminating Dangerous Lymphocytes," *Cell,* 84(5):655–657 (1996).

Blau, H.M., et al., "Gene Therapy—A Novel Form of Drug Delivery," *N. Engl. J. Med.,* 333(18):1204–1207 (1995).

Merten, O.W., et al., "A New Method for the Encapsulation of Mammalian Cells," *Cytotechnology* 7:121–130 (1991).

Chen, L. and Waxman, D.J., "Intratumoral Activation and Enhanced Chemotherapeutic Effect of Oxazaphosphorines following Cytochrome P–450 Gene Transfer: Development of a Combined Chemotherapy/Cancer Gene Therapy Strategy," *Cancer Research* 55:581–589 (Feb. 1, 1995).

King, G.A., et al., "Alginate Concentration: A Key Factor in Growth of Temperature–Sensitive Baculovirus–Infected Insect Cells in Microcapsules," *Biotechnol. Bioeng.,* 34:1085–1091 (1989).

Saller, R.M., et al., "Microcapsules Provide a Novel Alternative for Systemic Virus Release," *Gene Therapy,* 2(1):S12 (1995).

Stange, J., et al., "Prolonged Biochemical and Morphological Stability of Encapsulated Liver Cells—A New Method," *Biomat., Art. Cells & Immob. Biotech.,* 21(3):343–352 (1993).

Tai, I.T. and Sun, A.M., "Microencapsulation of Recombinant Cells: a new Delivery System for Gene Therapy," *FASEB J.,* 7:1061–1069 (1993).

Ram, Z., et al., "In Situ Retroviral–mediated Gene Transfer for the Treatment of Brain Tumors in Rats," *Cancer Res.,* 53:83–88 (1993).

Chang, P.L., "Nonautologous Somatic Gene Therapy," In *Somatic Gene Therapy,* Chang, P.L., ed., (CRC Press, Boca Raton), pp. 203–223 (1995).

Hughes, M., et al., "Delivery of a Secretable Adenosine Deaminase Through Microcapsules—A Novel Approach to Somatic Gene Therapy," *Human Gene Therapy,* 5:1445–1455 (1994).

Winn, S.R., et al., "Polymer–encapsulated Cells Genetically Modified to Secrete Human Nerve Growth Factor Promote the Survival of Axotomized Septal Cholinergic Neurons," *Proc. Natl. Acad. Sci., USA,* 91:2324–2328 (1994).

Déglon, N., et al., "Development of Gene Therapy for the Treatment of Neurodegenerative Diseases," *Gene Therapy,* 2:563 (1995).

Dautzenberg, H., et al., "Methods for a Comprehensive Characterization of Microcapsules Based on Polyelectrolyte Complexes," *Biomat. Art. Cells & Immob. Biotech.,* 21(3):399–405 (1993).

Culver, K.W., et al., "In Vivo Gene Transfer with Retroviral Vector–Producer Cells for Treatment of Experimental Brain Tumors," *Science,* 256:1550–1552 (1992).

\* cited by examiner

5'TGTTGCTTCTATGCGGACCA 3'
5'CCGCGCTTATTAGCCTGTTA 3'

ENCAPSULATED CELLS PRODUCING VIRAL PARTICLES

RELATED APPLICATIONS

This application is a continuation application of PCT/EP96/02748 which claims priority to Danish patent application DK 0740/95 filed Jun. 27, 1995. The contents of PCT/EP96/02748 and DK 0740/95 are incorporated herein by reference in their entirety.

BACKGROUND OF THE INVENTION

The delivery of genes of therapeutic benefit to target cells is central to the concept of gene therapy. If gene therapy is to become a routine procedure it is of utmost importance that systems are developed that allow effective in vivo delivery of therapeutic genes to the target cells.

Viral vectors, and especially retroviral vectors are the most commonly used delivery vehicles for gene therapy (Morgan, R. A. and Anderson, W. F., Ann. Rev. Biochem., 62:191–217, (1993)). Most of the currently approved gene therapy protocols take an ex vivo approach in that cells are removed from the patient, genetically modified in vitro and then reintroduced into the patient. This procedure is cumbersome, expensive and limited to technologically advanced facilities. Further this kind of approach is limited to cells that can easily be isolated, cultured and reimplanted (Günzburg, W. H., and Salmons, B., Biologicals, 23:5–12 or Günzburg, W. H., and Salmons, B., Molecular Medicine Today, 1:410–417 1995). Although an in vivo delivery of therapeutic genes would offer many advantages, in its present form this approach is both inefficient and problematic. A major problem, due to low efficiency of gene transfer, is the necessity for multiple applications of viral vector. The requirement for multiple rounds of vector delivery is not only tedious but also likely to be unsuccessful because of immune responses directed towards the virus particles.

One possible way in which these problems could be circumvented is through the direct implantation of cells producing viral particles. The implantation of cells producing viral particles containing the genome of a viral vector in situ next to the target organ or cells would also allow direct application of the viral vector to the target cells/organs.

Additionally, where the viral vector virus used is a retroviral virus, such an approach have an advantage over multiple single high dosage applications, since the chances of the vector virus being present at the time when a target cell undergoes replication, and thus being able to infect the target cell is increased. Furthermore a lower but continuous release of viral particles may be advantageous in escaping host immune response against the viral particle.

For an effective delivery of viral vectors, the cells producing viral particles should be able to survive long periods in the host after implantation, and viral particles must be produced during this period and released from the cells. In the absence of a significant immune response, for instance after implantation in the brain, these cells can survive over prolonged periods (Culver et al., Science, 256:1550–1552 (1992); Ram, Z. et al., Cancer Res., 53:83–88 (1993)). However to achieve successful implantation at other sites in the body, the producer cells must be protected from the immune system.

The long term effectivity of this approach thus depends on (1) protection of the cells from the host immune system, which will normally eliminate cells producing viral particles, especially if the cells producing the viral particles are from a different species as is usually the case for such cells and (2) survival of the cells in situ for extended periods, which may require vascularization.

Encapsulation of cells in permeable structures that allow the release of certain biologically active molecules but protects the cells producing these molecules from the host immune system has met with some success (for a review see Chang, P. L., In somatic Gene Therapy, P. L Chang, ed. (CRC Press, Boca Raton) p. 203–223 (1995)). Cells that have been genetically modified to produce human growth hormone (hGH) (Tai, I. T. and Sun, A. M. FASEB J., 7:1061–1069 (1993)) or a secreted form of human adenosine deaminase (Hughes, M. et al., Hum. Gene Ther., 5:1445–1455 (1994)) have been encapsulated. In both of these studies, cells were encapsulated in poly-L-lysine-alginate microcapsules and the cells were shown to survive for long periods in culture. This was accompanied by long term production of the enzyme or hormone. Further, it was shown (Tai, I. T. and Sun, A. M., FASEB J., 7:1061–1069 (1993)) that upon transplantation of the microcapsules into mice, the cells remained viable for 1 year and they continued to produce hGH, demonstrating that the capsules protect the transfected cells from destruction by the host immune system.

Cell encapsulation has also been reported using other materials. Baby hamster kidney cells genetically modified to produce nerve growth factor have been encapsulated in polyacrylonitrile/vinyl chloride and implanted in rat brain. The encapsulated cells survived for at least 6 months and continued to produce NGF (Winn, S. R. et al., Proc. Natl. Acad. Sci. USA, 91:2324–2328 (1994); Deglon, N. et al., Gene Ther., 2:563 (1995)).

Additionally, hepatocytes have successfully been encapsulated in a polyelectrolyte complex of cellulose sulphate and polydimethyldiallyl ammonium (Stange, J. et al., Biomat. Art. Cells & Immob. Biotech., 21:343–352 (1993)). More that 90% of the encapsulated hepatocytes retained their viability and in contrast to hepatocytes grown as monolayers, the encapsulated cells showed an increased metabolic activity. It is not suggested herein that cellulose sulphate/polydimethyldiallylammonium capsules could support the growth other types of cells, such as cells producing viral particles, or allow the exit of viral particles from such capsules.

The preparation of cellulose sulphate capsules used in the present invention has been thoroughly described in DE 40 21 050 A1. Also the synthesis of the cellulose sulphate has been described in this patent application. Methods for a comprehensive characterization of cellulose sulphate capsules have been extensively dealt with in H. Dautzenberg et al., Biomat., Art. Cells & Immob. Biotech., 21(3):399–405 (1993). Other cellulose sulphate capsules have been described in GB2 135 954. The properties of the cellulose capsules, i.e. the size, the pore size, wall thickness and mechanical properties depend upon several factors such as for example physical circumstances whereunder the capsules have been prepared, viscosity of precipitation bath, its ion strength, temperature, rapidity of addition of cell/cellulose sulphate suspension, constitution of cellulose sulphate, as well as other parameters described by the Dautzenberg group.

It has surprisingly been found that the continuous production of viral particles from implanted cells can be achieved by encapsulation of the cells in a polyelectrolyte complex. Although the pores of such capsules are large enough to allow antibodies and complement, known to inactivate virus (Welsh, R. M. et al., *Nature,* 257:612–614 (1975); Cornetta, K. et al., *Hum. Gene Ther.,* 1:15–30 (1990)), to enter the capsules, we have found no evidence of gross immune or inflammatory responses, or of necrosis in the vicinity of implanted capsules. Additionally, it has surprisingly been found that the capsules according to the present invention become well engrafted in the host, and become rapidly vascularized. The encapsulated cells according to the invention thus permits long term delivery of viral vectors carrying therapeutic genes in vivo.

SUMMARY OF THE INVENTION

The invention then, inter alia, comprises the following alone or in combination:

Encapsulated cells producing viral particles comprising a core containing cells; and a porous capsule wall surrounding said core, said porous capsule wall being permeable to said viral particles;

encapsulated cells as above wherein said porous capsule wall consists of a polyelectrolyte complex formed from counter-charged polyelectrolytes;

encapsulated cells as above wherein said porous capsule wall consists of a polyelectrolyte complex formed from sulphate group-containing polysaccharides or polysaccharide derivatives or sulphonate group-containing synthetic polymers and polymers with quaternary ammonium groups;

encapsulated cells as above wherein the sulphate group-containing polysaccharides or polysaccharide derivative is cellulose sulphate, cellulose acetate sulphate, carboxymethylcellulose sulphate, dextran sulphate or starch sulphate, and the sulphonate group-containing synthetic polymer is a polystyrene sulphonate;

encapsulated cells as above wherein the polymer with quaternary ammonium groups is polydimethyldiallylammonium or polyvinylbenzyl-trimethylammonium;

encapsulated cells as above wherein the porous capsule wall consists of a complex formed from cellulose sulphate and polydimethyldiallyl ammonium;

encapsulated cells as above having the form of microcapsules with a diameter between 0.01 and 5 mm, preferably between 0.1 and 1 mm;

encapsulated cells as any above wherein said capsule consist a spongy cellulose sulphate matrix forming the interior of the capsule wall, surrounded by a capsule surface containing pores; said spongy matrix being filled with cells;

encapsulated cells as above wherein the surface pore size of the porous capsule wall is between 80 and 150 nm, preferably between 100–120 nm;

encapsulated cells as above wherein the viral particle produced by the encapsulated cells is a retroviral particle containing the genome of a retroviral vector;

encapsulated cells as above wherein the encapsulated cells producing retroviral particles is a packaging cell line transfected with an expression vector, said expression vector carrying a retroviral vector construct capable of infecting and directing the expression in target cells of one or more coding sequences carried by said retroviral vector construct; said packaging cell line harboring at least one expression vector carrying genes coding for the proteins required for the retroviral vector construct to be packaged;

encapsulated cells as above wherein at least one of said coding sequences code for heterologous peptides selected from marker genes, therapeutic genes, antiviral genes, antitumor genes, and cytokine genes;

encapsulated cells as above wherein said marker gene is selected from the group consisting of marker genes which codes for proteins such as β-galactosidase, neomycin, alcohol dehydrogenase, puromycin, hypoxanthine phosphoribosyl transferase (HPRT), hygromycin and secreted alkaline phosphatase, and said therapeutic gene is selected from genes which codes for proteins such as Herpes Simplex Virus thymidine kinase, cytosine deaminase, guanine phosphoribosyl transferase (gpt), cytochrome P 450 and cell cycle regulatory genes such as SDI, tumour suppressor genes which codes for proteins such as p53 or antiproliferation genes which codes for proteins such as melittin, cecropin or cytokines such as IL-2;

encapsulated cells as above wherein the packaging cell line is selected from psi-2, psi-crypt, psi-AM, GP+E-86, PA317, and GP+envAM-12;

encapsulated cells as above wherein the expression vector transfected into the packaging cell line is pBAG, pLXSN, p125LX, pLX2B1, or pc3/2B1 or derivatives thereof;

a process for the preparation of encapsulated cells as above comprising suspending the cells providing viral particles in an aqueous solution of a polyelectrolyte, whereafter the suspension in the form of preformed particles is introduced into a precipitation bath containing an aqueous solution of a counter-charged polyelectrolyte;

a process as above wherein the particle formation takes place by spraying;

a process as above wherein the cells are suspended in an aqueous solution of a sulphate group-containing polysaccharide or polysaccharide derivative, or a sulphonate group-containing synthetic polymer;

a process as above wherein the sulphate group-containing polysaccharide or polysaccharide derivative is selected from cellulose sulphate, cellulose acetate sulphate, carboxymethylcellulose sulphate, dextran sulphate or starch sulphate, and the sulphonate group-containing synthetic polymer is a polystyrene sulphonate;

a process as above wherein the precipitation bath contain an aqueous solution of a polymer with quaternary ammonium groups;

a process as above wherein the polymer with quaternary ammonium groups is polydimethyldiallylammonium or polyvinylbenzyl-trimethylammonium;

a process as above wherein the cells are suspended in an aqueous solution of sodium cellulose sulphate, and introduced into a precipitation bath containing an aqueous solution of polydimethyldiallylammonium chloride;

a method as above wherein the aqueous cellulose sulphate solution is composed of 0.5–50%, preferably 2–5% sodium cellulose sulphate and 2–10%, preferably 5% fetal calf serum in buffered saline;

a method as above wherein the aqueous solution in the precipitation bath is composed of 0.5–50% preferably 2–10%, or more preferred 3% polydimethyldiallylammonium chloride in buffered saline;

encapsulated cells as any above produced by a process as above;

the use of the encapsulated cells as any above for the delivery of genes to target organ/cells comprising:
 a) Culturing the encapsulated cells in a suitable medium, and
 b) Implantation of the encapsulated cells into a living animal body, including a human;

the use as above wherein the target organ/cells is the mammary gland, or the pancreas; and the use as above wherein the target organ/cells are the smooth muscle cells and other cell types surrounding the arteries.

DETAILED DESCRIPTION OF THE INVENTION

Figure 1:
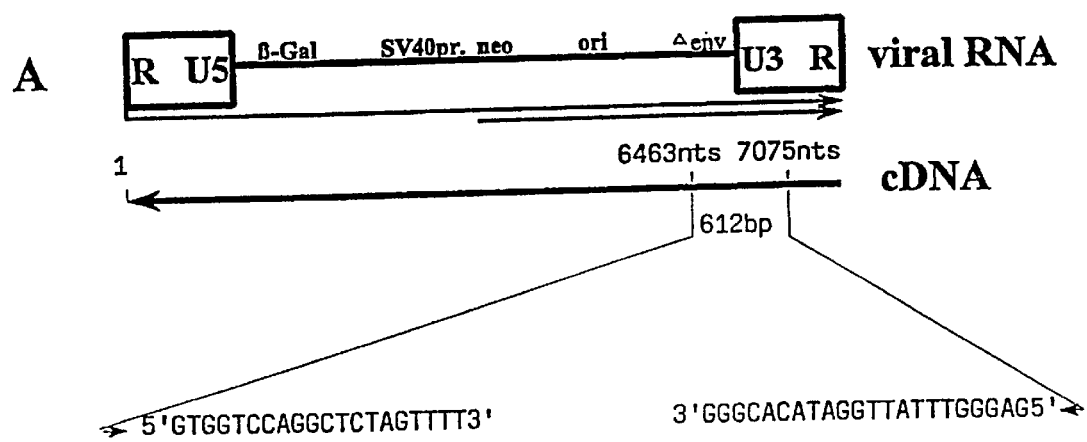
FIG. 1 is the MLV derived BAG vector.

It is an object of the present invention to provide encapsulated cells producing viral particles, which allow the release of the viral particles produced by the cells from the capsule, and at the same time do not elicit a significant host immune or inflammatory response after implantation in a host.

It is a further object of the present invention to provide a process for the production of such encapsulated cells producing viral particles.

Still an object of the present invention is to provide a method for the delivery of genes, especially therapeutic genes, to target organs/cells by implantation of such encapsulated cells producing viral particles in a host, and thereby provide for the continuous production and release of viral particles in the target organs or near target cells.

THE INVENTION

According to the present invention, encapsulated cells producing viral particles, which allow the release of the viral particles produced by the cells from the capsules, and at the same time do not elicit a significant host immune or inflammatory response after implantation in a host, are provided.

The encapsulated cells according to the invention can be prepared by suspending the cells producing viral particles in an aqueous solution of a polyelectrolyte (e.g., selected from sulphate group-containing polysaccharides or polysaccharide derivatives or of sulphonate group containing synthetic polymers), whereafter the suspension in the form of pre-formed particles is introduced into a precipitation bath containing an aqueous solution of a counter-charged polyelectrolyte (such as for example a polymer with quaternary ammonium groups).

Sulfate group-containing polysaccharides or polysaccharide derivatives includes cellulose sulfate, cellulose acetate sulfate, carboxymethylcellulose sulfate, dextran sulfate or starch sulfate in the form of a salt, especially a sodium salt. The sulfonate group-containing synthetic polymer can be a polystyrene sulfonate salt, preferably a sodium salt.

Polymers with quaternary ammonium groups includes polydimethyldiallylammonium or polyvinylbenzyl-trimethylammonium, in the form of a salt thereof, preferably a chloride salt.

In a preferred embodiment of the invention the cells producing viral particles are encapsulated in a complex consisting of a complex formed from cellulose sulfate and polydimethyldiallyl-ammonium.

Such capsules are preferably prepared by suspending the cells producing viral particles in a solution containing 0.5–50%, preferably 2–5%, sodium cellulose sulfate and 5% fetal calf serum optionally in buffer. This suspension is then dropped by a dispensing system (e.g., air-jet system or piezoelectric system) while stirring into a precipitation bath containing 0.5–50%, preferably 2–10%, or most preferred around 3% polydimethyl-diallylammonium chloride optionally in buffer. Capsule formation occurs within milliseconds and the capsules containing cells are kept in the precipitation bath for 30 seconds to 5 minutes and then washed. The rapidity of this method ensures that the cells are not unduly stressed during the whole procedure (Stange, J. et al., *Biomat. Art. Cells & Immob. Biotech.*, 21:343–352 (1993)).

The capsules according to the invention have a variable diameter between 0.01 and 5 mm, but are preferably between 0.1 and 1 mm. Consequently, capsules can be made to contain a variable number of cells. Using the encapsulation process according to the invention, up to $10^{10}$, but preferably $10^5$–$10^7$ cells producing viral particles can be encapsulated in the polyelectrolyte complex.

Capsules composed of cellulose sulfate and polydimethyldiallyl ammonium have excellent mechanical properties and can be manufactured to consistent size and pore size.

The pore size of the capsules is between 80 and 150 nm, preferably between 100 and 120 nm.

The encapsulated cells can be cultivated in a normal cell culture medium (the nature of which depends on the encapsulated cells) at standard conditions of humidity, temperature and $CO_2$ concentration. During this culture period production of viral particles from the capsules into the cell culture medium can be demonstrated using either RT-PCR technology or by transfer of cell free (0.45 $\mu$m filtered) supernatant to target cells followed by the demonstration of viral infection by assay for the activity of marker proteins encoded by genes carried by the viral vector construct contained within the viral particle. If the marker gene carried by the viral vector is a gene conferring resistance to a specific compound upon the target cell, the titre of virus produced by the system can be ascertained.

After a suitable period in culture (normally not less than 1 hour and not exceeding 30 days), the cell containing capsules can be surgically implanted either directly, or by injection using a syringe into various areas of the body.

The viral particles produced by the encapsulated cells according to the invention can be based on any virus useful for gene therapy, including but not limited to adenoviruses, adenovirus associated viruses, herpes viruses or retroviruses; for a review see Günzburg, W. H., and Salmons, B., *Molecular Medicine Today*, 1:410–417 (1995).

In a preferred embodiment of the invention, the encapsulated cells is a packaging cell line producing retroviral particles containing the genome of a retroviral vector construct carrying marker and/or therapeutic genes.

Retroviral Vector Systems Consist of Two Components 1) an expression vector (vector plasmid) carrying a retroviral vector construct which is a modified retrovirus in which the genes encoding for the viral proteins have been replaced by therapeutic genes optionally including marker genes to be transferred to the target cell. Since the replacement of the genes encoding for the viral proteins effectively cripples the virus it must be rescued by the second component in the system which provides the missing viral proteins to the modified retrovirus.

The second component is:

2) a cell line that produces large quantities of the viral proteins, however lacks the ability to produce replication competent virus. This cell line is known as the packaging cell line and consists of a cell line transfected with plasmids carrying the genes enabling the modified retroviral genome to be packaged. These plasmids direct the synthesis of the necessary viral proteins required for virion production.

To generate the packaged retroviral vector, the vector plasmid is transfected into the packaging cell line. Under these conditions the modified retroviral genome including the inserted therapeutic and optional marker genes is transcribed from the vector plasmid and the resulting modified retroviral genome is packaged into the retroviral particles. A cell infected with such a viral particle cannot produce viral particles since no viral proteins are present in these cells. However the retroviral vector construct carrying the therapeutic and marker genes is present and these can now be expressed in the infected cell.

WO 94/29437, WO 89/11539 and WO 96/07748 describe different types of retroviral vector systems useful for the purpose of the present invention.

The viral particles produced by the encapsulated cells according to the invention, can be constructed to contain the genome of a viral vector carrying genes encoding marker and/or therapeutic genes.

The marker or therapeutic genes carried by the viral vector can be, for example, genes which code for proteins such as β-galactosidase, neomycin, alcohol dehydrogenase, puromycin, hypoxanthine phosphoribosyl transferase (HPRT), hygromycin and secreted alkaline phosphatase or therapeutic genes which code for proteins such as Herpes Simplex Virus thymidine kinase, cytosine deaminase, guanine phosphoribosyl transferase (get), cytochrome P 450, cell cycle regulatory genes such as SDI, tumour suppressor genes which code for proteins such as p53, antiproliferation genes which code for proteins such as melittin, cecropin or cytokines such as IL-2.

In a special embodiment, the invention relates to the use of the encapsulated cells according to the invention in the treatment of tumours.

Many malignant tumours do not respond well to chemotherapy. The anti-cancer drugs used to treat tumours are in most cases applied systemically and therefore spread through the whole body of the patient. The high systemic dose of such drugs required for cancer treatment often is combined with unpleasant side-effects for the patient. One strategy by which these problems of high systemic concentration of anti-cancer drugs could be circumvented is by the direct application or by the activation of the drug directly in or near the tumour. This could be achieved by implantation of encapsulated cells according to the invention producing viral particles containing the genome of an engineered virus, especially a retroviral vector, carrying a gene encoding an anti-cancer drug, for example an activating enzyme capable of converting a prodrug to a cytotoxic agent, either into tumour cells or into nearby cells.

In one embodiment of the invention encapsulated cells producing retroviral particles containing the genome of a retroviral vector carrying tumour relevant enzymes such as cytochrome P450 or suicide genes such as but not limited to thymidine kinase which convert non-toxic drugs to one or more toxic metabolites are provided. Such encapsulated cells of the invention can be used for the treatment of cancer by implantation of the capsules in or near the tumours, e.g., tumours in the pancreas or the mammary gland.

Additional targeting can be obtained by the use of target cell specific regulatory elements and promoters for the direction of the expression of linked therapeutic genes to specific cell types.

Such target cell specific regulatory elements and promoters include, for example, pancreas specific regulatory elements and promoters including carbonic anhydrase II and β-glucokinase regulatory elements and promoters; lymphocyte specific regulatory elements and promoters including immunoglobulin and MMTV lymphocytic specific regulatory elements and promoters; mammary specific regulatory elements and promoters including Whey Acidic Protein (WAP), Mouse Mammary Tumour Virus (MMTV), β-lactoglobulin and casein specific regulatory elements and promoters and MMTV specific regulatory elements and promoters conferring responsiveness to glucocorticoid hormones or directing expression to the mammary gland. Other promoters include for example the CD4, CD34, and IL2 promoters. Said regulatory elements and promoters regulate preferably the expression of said retroviral vector.

Inducible promoters such as radiation inducible promoters, for example, the intercellular adhesion molecule-1 (ICAM-1) promoter, the epidermal growth factor receptor (EGFR) promoter and the tumour necrosis factor (TNF) promoter can also be used.

The following examples will illustrate the invention further, however they are not to be construed as limiting:

EXAMPLE 1

Lipofection of PA317 with pBAG, and Isolation of G418 Resistant Cells

Amphotropic NIH3T3 based PA317 packaging cells (Miller, A. D. and Buttimore, C., *Mol. Cell. Biol.*, 6:2895–2902 (1986)) were cultured in Dulbecco's modified Eagle's medium (DMEM) containing 10% fetal calf serum. The cells were seeded in a 10 cm tissue culture dish at a density of $3\times10^5$ cells one day prior to lipofection and then lipofected with 2 µg of pBAG vector (Price, J. et al., *Proc. Natl. Acad. Sci. USA*, 84:156–160 (1987)) carrying a MLV (Mouse Leukemia Virus) based retroviral vector using the lipofectamine kit from GIBCO/BRL according to the manufacturers' instructions. The cells were then diluted one to ten and cultured in the usual medium containing additionally 400 µg/ml G418 (GIBCO/BRL). After 14 days colonies of G418 resistant cells were pooled.

EXAMPLE 2

Microencapsulation $10^7$ cells were suspended in 1 ml of a buffered saline solution containing 2–5% sodium cellulose sulfate and 5% fetal calf serum and the suspension dropped using a dispensing system (air-jet system) into a precipitation bath containing 2–3% polydimethyl-diallylammonium in buffered saline. Capsule formation occurred within milliseconds followed by further constitution of an inner, more porous, layer for mechanical support essentially consisting of cellulose sulfate. The capsule containing cells are kept in the precipitation bath for 30 seconds to 5 minutes and then washed in DMEM (Stange, J. et al., *Biomat. Art. Cells & Immob. Biotech.*, 21:343–352 (1993)). Batches obtained to different parameters as described above, i.e., concentration of sodium cellulose sulfate, flow of air-jet system and time in precipitation bath were used for biological studies. Representative examples of conditions are for example: 2.5% sodium cellulose sulfate, 2% polydimethyl-diallylammonium, and 1 minute in precipitation bath, or 1.5% sodium cellulose sulfate, 2% polydimethyl-diallylammonium, and 0.5 minute in precipitation bath, or 3% sodium cellulose sulfate, 3% polydimethyl-diallylammonium, and 2 minute in precipitation bath. The exact parameters are selected also taking into account the exact size of the capsules wanted, the thickness of the capsule wall as well as other properties.

EXAMPLE 3
Implantation of Microcapsules into the Mammary Gland of Mice

The microcapsules were inserted into the mammary gland of female 2 month old BALB/c mice by "key hole" surgery and the entry site closed by 1 suture. Up to six capsules of 0.5–2 mm diameter were inserted at each operation site.

In vitro studies of virus release from the microcapsules, the structure of the microcapsules and the effect of the capsule implantation into immunocompetent mice were studied using the following test methods:

A) β-galactosidase Activity

Detection of infected cells by histochemical staining was performed as outlined previously (Cepko, C., *Meth. Neurosci.*, 1:367–392 (1989)). The cells, capsules or tissue sections were washed with chilled PBS and then fixed with a 2% paraformaldehyde solution for 20 minutes–24 hours according to the thickness of the sample. After extensive washing with PBS, the cells, capsules or tissue sections were incubated in a solution containing the substrate X-gal (20 mM $K_3FeCN_6$, 20 mM $K_4FeCN_6.3H_2O$, 2 mM $MgCl_2$ and 1 mg/ml X-gal) for at least 2 hours at 37° C.

B) Infection $4 \times 10^4$ target cells were seeded in 6-well tissue culture plates 6 hours prior to infection. Capsules containing virus producing cells were placed on top of the cells and polybrene (8 µg/ml) was added to the medium. Four hours later the medium was exchanged to remove the residual polybrene. Five day later some wells were stained for β-galactosidase activity as described above, the others were trypsinized into larger tissue culture dishes and cultured in media containing 400 µg/ml G418. Sixteen days later G418 resistant colonies were detected.

C) RT-PCR Analysis of Virus Particles Released by the Capsules

Virus particles from 5 ml of capsule culture medium supernatant were pelleted by ultracentrifugation (240,000× g, 1 hour, 4° C.). The pellet was resuspended in lysis buffer (1% Triton 100, 0.5% sodium desoxycholate, 0.1% sodium dodecyl sulfate, PBS) and the RNA extracted by phenol extraction followed by ethanol precipitation, as previously described (Salmons, B. et al., *Virus Res.*, 4:377–389 (1986)). The RNA was then reverse transcribed into DNA using the Ready-To-Go T-primed first-strand kit (Pharmacia). PCR amplification was performed using primers, 5' GTGGTC-CAGGCTCTAGTTTT 3' (SEQ ID NO:1) and 3' GGGCA-CATAGGTTATTTGGGAG 5' (SEQ ID NO:2), located within the env and the R of the MLV derived BAG vector LTR (FIG. 1). The PCR amplification was performed in 100 µl reaction mixtures consisting of 500 mM KCl, 10 mM Tris-HCl(pH8.3) 1.5 mM $MgCl_2$, 0.01% (w/v) gelatine and 100 µM of each dNTP, 40 pM of each primer and 2.5 units Taq polymerase (Perkin Elmer). The reactions were performed in a Perkin Elmer Cetus Therma cycler 9600 under the following conditions: 1 minute at 94° C., 2 minutes at 53° C. and 3 minutes at 72° C. for 35 cycles. The PCR products were separated on a 0.8% agarose gel and then they were transferred to Zeta probe membranes (BIORAD) and hybridized, as previously described (Indraccolo, S. et al., *Mammalian Genome*, 6:339–344 (1995)), to a $^{32}$P-labeled 612 bp PCR fragment of the MLV genome generated using the same primers and pBAG as a template. MLV specific sequences were visualized using a Fuji phosphoimaging system (BAS 1000).

Medium was taken after 2, 3, 5 and 6 weeks culture of capsules. Cell culture medium from nonencapsulated BAG virus producing cells was used as positive control and medium from nontransfected PA317 as negative control. No signals were observed when the viral samples were digested with RNase before performing the RT-PCR analysis to ensure that the amplified band was derived from viral RNA. Viral RNA prepared from nonencapsulated BAG virus producing cells, without RNase treatment, was used as a positive control in the RT-PCR reaction.

D) PCR Analysis

Genomic DNA (1 µg) was amplified by PCR using one primer located within the residual env sequences of the BAG vector and a second primer in the polyoma region of the plasmid outside of the retroviral vector sequences. PCR reactions were performed as described above using the following reaction conditions: 1 minute at 94° C., 2 minutes at 50° C. and 3 minutes at 68° C. for 35 cycles. The PCR product was hybridized with a $^{32}$P-labeled 1.5 kb XbaI DNA fragment from pBAG that is specific for the polyoma sequences.

E) Electron Microscopy

The specimens for scanning electron microscopy (SEM) and transmission electron microscopy (TEM) examination were rinsed in PBS (pH 7.35) and prefixed in 1% glutaraldehyde in PBS for 15 minutes before postfixing in 2% $OsO_4$ for 15 minutes. The samples were dehydrated in a graded series of ethanol and then divided into two groups.

a) The SEM samples were critical-point-dried using $CO_2$ and coated with 1–3 nm platinum (Emscope SC 500; Ashford, England). The coated specimens were examined in a 10 kV field emission scanning electron microscope (Joel JSM-6300F; Tokyo, Japan), with accelerating voltages of 5–10 kV in secondary mode.

b) The TEM samples were embedded in Epon. Ultrathin sections were double stained with uranyl acetate and lead citrate, and viewed in a Zeiss EM-10C (Oberkochen, Germany) transmission electron microscope.

Results

In vitro studies of virus release from the microcapsules:

Staining of the cells in the microcapsules obtained in Example 2 with the substrate X-gal as described in the above test for β-galactosidase activity for revealed that they expressed the β-galactosidase gene encoded by pBAG, as do nonencapsulated vector producing cells. Histological staining of encapsulated PA317 cells stably transfected with pBAG demonstrate β-galactosidase expression.

To demonstrate that virus particles are released from the cells in the microcapsules into the cell culture medium, RNA was prepared from pelleted virions harvested from capsule supernatants after various time periods in culture. This RNA was analyzed by RT-PCR using primers complementary to the viral env and R regions as described under RT-PCR analysis above. An MLV specific, PCR generated, fragment of the expected size (612 bp) was observed in the microcapsule culture medium for at least 6 weeks, at which point analyses were discontinued. This fragment is not due to contaminating DNA since pre-treatment of the viral RNA with RNase prior to RT-PCR resulted in no signal.

Production and release of infectious virus from the capsules could be verified by their co-cultivation as described under the test infection above with target cells, e.g., NIH3T3 (Jainchill, J. L. et al., *J. Virol.*, 4:549–553 (1969)) or CRFK (Crandell, R. A. et al., *In vitro*, 9:176–185 (1973)) cells. Target cells were seeded at low density one day before capsules containing retroviral vector producing packaging cells were added. Both cells and capsules were stained histologically for β-galactosidase activity several days later. After 4 days co-cultivation, an aliquot of the target cells as well as the encapsulated packaging cells were stained for β-galactosidase activity as described above. The remaining target cells were selected for G418 resistance. Many of the co-cultured NIH3T3 and CRFK cells could be shown to express the β-gal gene.

Figure 2:
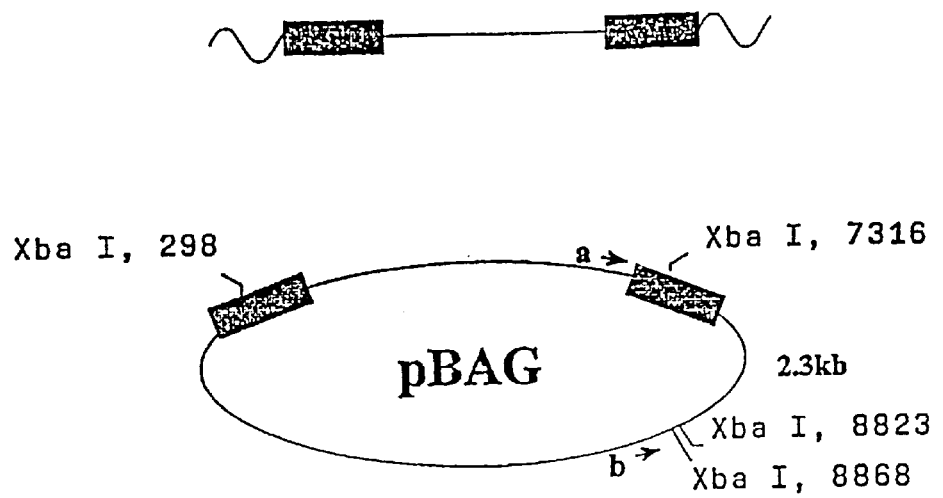
FIG. 2 is a schematic of the plasmid pBAG and integrated BAG after infection.

In order to verify that the β-galactosidase expressing target cells were derived from an infection event rather than by the escape of virus producing cells, genomic DNA was extracted from cells and PCR analysis was performed. To confirm that the target cells had acquired the β-gal gene by infection, target cells were tested by PCR using primers 5' TGTTGCTTCTATGCGGACCA 3' (SEQ ID NO:3) and 5' CCGCGCTTATTAGCCTGTTA 3' (SEQ ID NO:4). The BAG producing packaging cell line is based upon the PA317 cell line (Miller, A. D. and Buttimore, C., *Mol. Cell Biol.,* 6:2895–2902 (1986)) and carries the thymidine kinase gene of Herpes Simplex virus (HSV-TK), the product of which converts the prodrug ganciclovir into a cytotoxic drug. The target NIH3T3 or CRFK cells do not normally carry this gene. In an experiment where it could be demonstrated that the β-gal expressing co-cultured NIH3T3 and CRFK target cells were resistant to GCV indicating that no escape of BAG producing cells had taken place, genomic DNA was extracted form the target cells and analyzed for presence of plasmid sequences outside the vector by PCR (PCR analysis above). These sequences (2.3 kb) are present in the packaging cells since the BAG vector was lipofected into these cells in the form of the plasmid pBAG (FIG. 2). However the virus produced from the packaging cells does not carry these plasmid sequences and so they should not be present in the target infected cells. The data demonstrated that no such plasmid sequences were detectable, compatible with infection of these cells with the BAG vector.

Structure of the Microcapsules

Sections of the microcapsules were prepared and their structure analyzed by electron microscopy. Scanning electron microscopy showed the surface of the capsule in which pore like structures become detectable at high power magnification (×75,000). The diameter of a retrovirus particle was 100 nm, indicating that the structures represented the pores through which the virus is released from the capsule. The interior of the capsule consisted of a spongy like matrix which was filled with cells. Scanning electron microscopy of the surface of the microcapsules revealed the presence of pores large enough to allow the passage of retroviral vector particles out of the capsules since the average diameter of a retrovirus particle was 100 nm.

In vivo Stability in Immunocompetent Mice

To determine the in vivo stability of the microcapsules and whether the microcapsules or the virus that they produce elicit a gross immune response, they were implanted into the mammary gland of female 2 months old BALB/c mice. The mice were sacrificed at various times after implantation to assess both the fate of the microcapsules and whether infectious virus was produced. Implanted microcapsules could be clearly seen embedded within the mammary fat pad for at least 6 weeks after implantation based on a histological analysis. Intriguingly, vascularization occurred within the vicinity of the microcapsules in all animals analyzed, presumably as a result of the production of angiogenic or growth factors by the packaging cells.

Light microscopy sections made through the microcapsule and surrounding mammary tissue after implantation into mouse mammary gland for four weeks (133 fold magnification) confirmed that blood vessels could be found in the immediate vicinity of the capsules. These sections also revealed a layer of connective tissue located between the microcapsule and the mammary tissue. There was no evidence of a gross inflammatory or immune response against the microcapsules or the virus producing cells that they contain.

In order to demonstrate that infectious retroviral vector particles had been released from the capsule and had infected the surrounding mammary tissue, some of the sections were analyzed for expression of β-gal by X-gal staining. The results showed infection of mouse mammary cells after implantation of BAG vector producing PA317 cell containing capsules. Cells expressing the β-gal gene were clearly visible outside of the microcapsule.

EXAMPLE 4

This example describes the construction of a retroviral expression vector for intratumoral infection which contains the gene for rat cytochrome P450 2B1.

Figure 3:
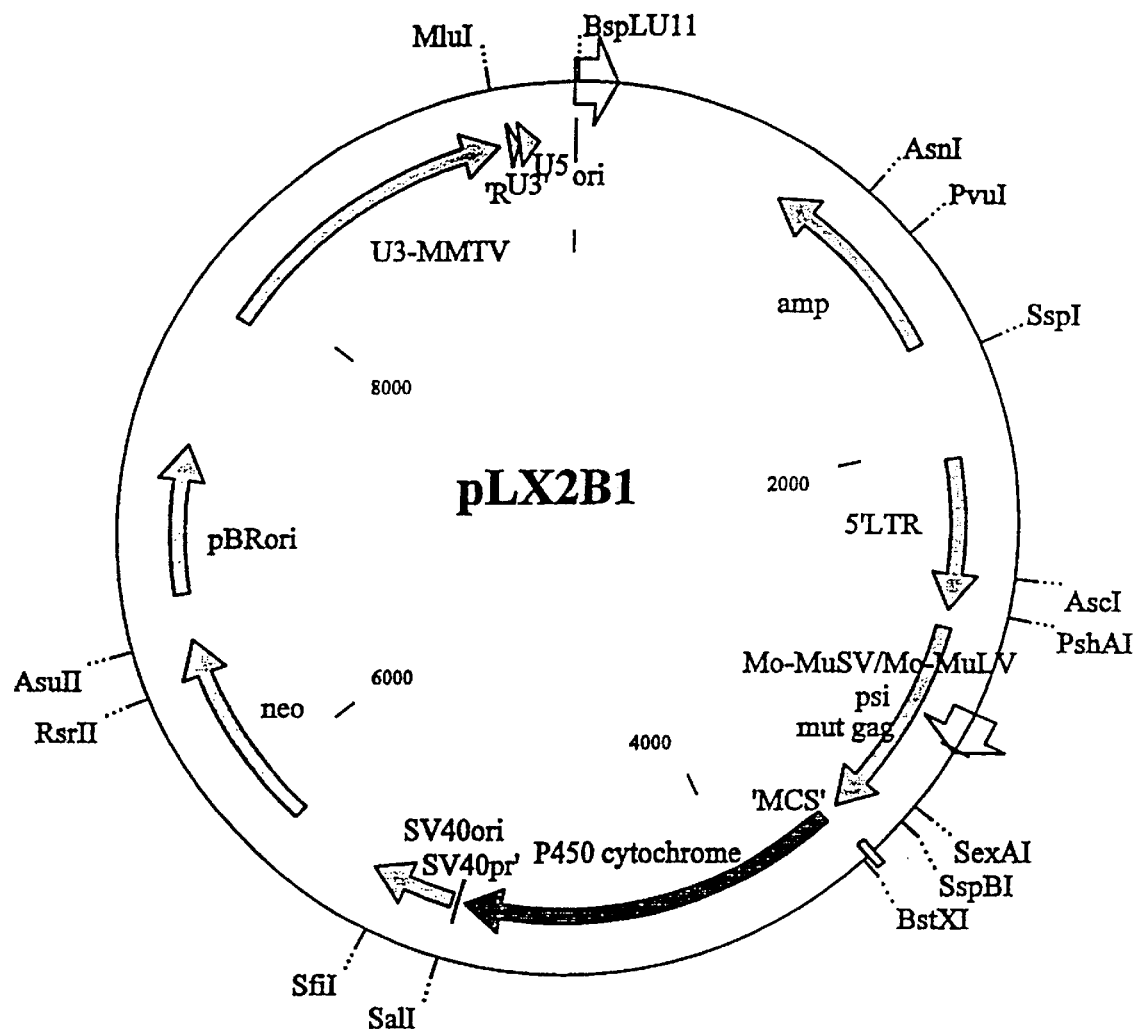
FIG. 3 is a schematic of the structure of the expression vector pLX2B1 containing the gene for rat cytochrome P450 2B1 which will be controlled by the U3-MMTV promoter after promoter conversion.

Expression vector pLX2B1, shown in FIG. 3, was constructed by ligation of fragments obtained from plasmid pLX125 and pSW1 (Kedzie, K. M. et al., *J. Biol. Chem.,* 266(33):22515–22521 (1991)). The plasmid pLX125 was linearized with HpaI and the resulting blunt ends dephosphorylated using calf intestine phosphatase. The DNA was purified by separation on a 1% agarose gel, excision and preparation using the Qiaquick protocol (Qiagen). After ethanol precipitation the DNA was resuspended in water.

The cloning vector pSW1 was digested with SmaI and HincII to yield two blunt ended fragments. The digestion mixture was separated on a 1% agarose gel. The shortest fragment (1.5 kb) containing the rat cytochrome P450 2B1 cDNA (Fuji-Kuriyama, Y. et al., *Proc. Natl. Acad. Sci. USA,* 79:2793–2797 (1982)) was excised and eluted using the Qiaquick DNA extraction protocol, ethanol precipitated and resuspended in water.

7.6 fMols of pLX125 and 24 fMols and the SmaI/HindII-fragment of pSW1 were mixed together and ligated for 3 days at 12° C. using T4-ligase (Boehringer). The ligase was inactivated at 65° C. for 10 minutes and the DNA butanol precipitated with a 10 fold volume of butanol. The precipitated DNA was resuspended in water and electroporated into DH10B-bacteria (Gibco). Ampicillin resistant colonies were selected, DNA prepared and test digested with SspBI/SalI, BamHI/SspBI, PvuI and BamHI. The final correct plasmid was designated pLX2B1.

Lipofection

One day before lipofection 3×10$^5$ retroviral packaging cells PA317 (Miller, A. D. and Buttimore, C., *Mol. Cell. Biol.,* 6:2895–2902 (1986)) were seeded into 6 cm petri or culture dishes. On the day of infection 2 μg of pLX2B1 were mixed with 100 μl serum free media. In parallel 15 μl of Lipofectamine (Gibco BRL) was mixed with 100 μl serum-free media. The plasmid containing solution was added to the Lipofectamine-mix and incubated for 45 minutes. After 35 minutes the cell were washed once with 2 ml serum free media. 800 μl of serum free media were added to the lipofection-mix and the resulting 1 ml was put onto the prepared cells. After 6 hours 1 ml Dulbecco's modified Eagles medium containing 10% FCS was added. The next day the cells were trypsinized and 1:10 diluted and seeded on a 100 mm dish. After 24 hours the media was replaced with medium containing the neomycin analogue G418. Single cell clones or cell populations were isolated and analyzed for expression of cytochrome P450.

Encapsulated

The retroviral vector producing packaging cells obtained are encapsulated as described in Example 2 above.

Implantation

The capsules obtained are introduced by "key hole" surgery near or in either transplanted or spontaneous tumours of BALB/c or GR mice. About six capsules of 1 mm diameter are inserted at each operation site. The site of surgery is closed by 1 suture. The mice are then treated with cyclophosphamide or ifosphamide locally, by direct intra-tumoral injection of 100 µl of 20 mg/ml or systemic concentrations of 130 mg CPA/kg body weight i.p. and 40–60 mg IFO/kg body weight i.p. for up to a maximum of 10 weeks. During this period tumour size and macroscopic appearance is monitored daily. The mice are then sacrificed, the tissue containing the inserted capsules and tumour removed, and histological sections for light and electron microscopy prepared. These sections clearly show good engraftment of the capsules, vascularization, and no evidence of the presence of lymphocytes indicative of a cellular immune response. These sections also show no sign of cell death or necrosis within the capsule. In contrast the tumour showed necrosis and macroscopically there was a clear reduction in size over the test period.

EXAMPLE 5

This example describes the construction of a stable cell line which expresses rat cytochrome P450 2B1 constitutively.

Expression vector pc3/2B1 was constructed by ligation of fragments obtained from plasmid pcDNA3 (Invitrogen) and pSW1 (Kedzie, K. M. et al., *J. Biol. Chem.*, 266(33): 22515–22521 (1991)).

The plasmid pcDNA3 was digested with XhoI/XbaI and the resulting sticky ended fragments dephosphorylated using calf intestine phosphatase. The DNA of the vector backbone was purified by separation on a 1% agarose gel, excision and preparation using the Qiaquick protocol (Qiagen). After ethanol precipitation the DNA was resuspended in water.

The cloning vector pSW1 was digested with XhoI and XbaI to yield two fragments. The digestion mixture was separated on a 1% agarose gel. The shortest fragment (1.5 kb) containing the rat cytochrome P450 2B1 cDNA (Fuji-Kuriyama, Y. et al., *Proc. Natl. Acad. Sci. USA*, 1982, 79:2793–2797 (1982) was excised and eluted using the Qiaquick DNA extraction protocol, ethanol precipitated and resuspended in water.

8.3 fMols of the pcDNA3 backbone and 24.8 fMols of the XhoI/XbaI-fragment of pSW1 were mixed together and ligated for 1 day at 12° C. using T4-ligase (Boehringer). The ligase was inactivated at 65° C. for 10 minutes and the DNA butanol precipitated with 10 fold volume of butanol. The precipitated DNA was resuspended in water and electroporated into DH10B-bacterial (Gibco). Ampicillin resistant colonies were selected, DNA prepared and test digested with EcoRI, BamHI, EcoRV and XhoI. The final correct plasmid was designated pc3/2B1

Lipofection

Before the day of infection $3 \times 10^5$ NIH3T3 cells were seeded into 35 mm dishes. On the day of infection 2 µg of pc3/2B1 was mixed with 100 µl serum free media. In parallel 15 µl Lipofectamine was mixed with 100 µl serum-free media. The plasmid containing solution was added to the Lipofectamine-mix and incubated for 45 minutes. After 35 minutes the cells were washed once with 2 ml serum free media. 800 µl of serum free media were added to the lipofection-mix and the resulting 1 ml was put onto the prepared cells. After 6 hours 1 ml DMEM (Glutamax) with 10% FCS were added. The next day the cells were trypsinized and diluted by factor ten and seeded on a 100 mm dish. After 24 hours the media was replaced against neomycin media. After 14 days neomycin resistant clones were isolated and tested for presence and activity of the vector.

Capsules containing these cells were produced as described in Example 2 and implanted in mice near the tumour site. After treatment with cyclophosphamide or ifosfamide the efficacy of treatment was evaluated as described above.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. Encapsulated retroviral packaging cells producing retroviral particles, comprising capsules having a porous capsule wall which is permeable to said retroviral particles.

2. The encapsulated cells according to claim 1 wherein said porous capsule wall comprises of a polyelectrolyte complex formed from counter-charged polyelectrolytes.

3. The encapsulated cells according to claim 1 wherein said porous capsule wall comprises a polyelectrolyte complex formed from sulphate group-containing polysaccharides or polysaccharide derivatives or sulphonate group-containing synthetic polymers and polymers with quaternary ammonium groups.

4. The encapsulated cells according to claim 3 wherein the sulphate group-containing polysaccharides or polysaccharide derivative are selected from one or more elements of the group consisting of: cellulose sulphate, cellulose acetate sulphate, carboxymethylcellulose sulphate, dextran sulphate or starch sulphate, and wherein the sulphonate group-containing synthetic polymer is a polystyrene sulphonate.

5. The encapsulated cells according to claim 3 wherein the polymer with quaternary ammonium groups is polydimethydiallylammonium or polyvinylbenzyl-trimethylammonium.

6. The encapsulated cells according to claim 1 wherein the porous capsule wall comprises a complex formed from cellulose sulphate and polydimethydiallyl-ammonium.

7. The encapsulated cells according to claim 1 having the form of microcapsules with a diameter between 0.01 and 5 mm, preferably between 0.1 and 1 mm.

8. The encapsulated cells according to claim 1 wherein said capsule comprises a spongy matrix forming the interior of the capsule surrounded by the capsule wall containing pores; said spongy matrix being filled with said cells.

9. The encapsulated cells according to claim 1 wherein the surface pore size of the porous capsule wall is between 80 and 150 nm, preferably between 100–120 nm.

10. The encapsulated cells according to claim 1 wherein the retroviral particle produced by the encapsulated cells is a retroviral particle containing the genome of a retroviral vector.

11. The encapsulated cells according to claim 1 wherein the encapsulated cells producing retroviral particles are a packaging cell line transfected with an expression vector, said expression vector carrying a retroviral vector construct capable of infecting and directing the expression in targets cells of one or more coding sequences carried by said retroviral vector construct; said packaging cell line harboring at least one expression vector carrying genes coding for the proteins required for the genome of said retroviral vector construct to be packaged.

12. The encapsulated cells according to claim 11 wherein at least one of said coding sequences code for heterologous peptides selected from marker genes, therapeutic genes, antiviral genes, antitumour genes, and cytokine genes.

13. The encapsulated cells according to claim 12 wherein said marker gene codes for a protein selected from the group consisting of: β-galactosidase, neomycin, alcohol dehydrogenase, puromycin, hypoxanthine phosphoribosyl transferase (HPRT), hygromycin and secreted alkaline phosphatase, and said therapeutic gene codes for a protein selected from the group consisting of: Herpes Simplex Virus thymidine kinase, cytosine deaminase, guanine phosphoribosyl transferase (gpt), cytochrome P450, a cell cycle regulatory protein, SDI, a tumour suppressor protein, p53, an antiproliferation protein, melittin, cecropin, a cytokine and IL-2.

14. The encapsulated cells according to claim 11 wherein the packaging cell line is selected from psi-2, psi-crypt, psi-AM, GP+E-86, PA317, and GP+envAM-12.

15. The encapsulated cells according to claim 11 wherein the expression vector is selected from the group consisting of: pBAG, pLXSN, p125LX, pLX2B1, pc3/2B1.

16. A process for preparing encapsulated retroviral packaging cells which produce retroviral particles, comprising capsules having a porous capsule wall which is permeable to said retroviral particles, comprising suspending the cells producing retroviral particles in an aqueous solution of polyelectrolyte, whereafter the suspension in the form of preformed particles is introduced into a precipitation bath containing an aqueous solution of a counter-charged polyelectrolyte.

17. A process according to claim 16 wherein particle formation takes place by spraying.

18. A process according to claim 16 wherein the cells are suspended in an aqueous solution of a sulphate group-containing polysaccharide or polysaccharide derivative, or a sulphonate group-containing synthetic polymer.

19. A process according to claim 18 wherein the sulphate group-containing polysaccharide or polysaccharide derivative is selected from cellulose sulphate, cellulose acetate sulphate, carboxymethylcellulose sulphate, dextran sulphate or starch sulphate, and the sulphonate group-containing synthetic polymer is a polystyrene sulphonate.

20. A process according to claim 16 wherein the precipitation bath contain an aqueous solution of a polymer with quaternary ammonium groups.

21. A process according to claim 20 wherein the polymer with quaternary ammonium group is polydimethyldiallylammonium or polyvinylbenzyl-trimethylammonium.

22. A process according to claim 16 wherein the cells are suspended in an aqueous solution of sodium cellulose sulphate, and introduced into a precipitation bath containing an aqueous solution of polydimethyldiallylammonium chloride.

23. A method according to claim 22 wherein the aqueous solution of sodium cellulose sulphate is composed of 0.5%–50%, preferably 2–5% sodium cellulose sulphate and 2–10%, preferably 5%, fetal calf serum in buffered saline.

24. A method according to claim 22 wherein the aqueous solution in the precipitation bath is composed of 0.5–50%, preferably 2–10%, or more preferred 3% polydimethyldiallylammonium chloride in buffered saline.

25. Encapsulated cells produced by a process according to claim 16.

26. A method for delivery of a gene into or close to the site of a target organ or cell wherein the gene is expressed comprising:
   a) culturing encapsulated retroviral packaging cells which produce retroviral particles, comprising capsules having a porous capsule wall which is permeable to said retroviral particles wherein the genome of the retroviral particles express the expression product of the gene, in a suitable medium, and
   b) locally administering the encapsulated cells into or near the site of the target organ or cell of a living animal body, including a human
   wherein infectious retroviral particles are produced and released from the capsules and the retroviral particles infect the target organ or cell, thereby delivering the gene to the target organ or cell wherein the gene is expressed.

27. The method according to claim 26 wherein the target organ or cell is a mammary gland, or a pancreas.

28. The method according to claim 26 wherein the target organ or cell are smooth muscle cells surrounding arteries.

* * * * *

UNITED STATES PATENT AND TRADEMARK OFFICE
CERTIFICATE OF CORRECTION

PATENT NO.   : 6,776,985 B1
DATED        : August 17, 2004
INVENTOR(S)  : Robert Michael Saller, Walter H. Günzburg and Brian Salmons It is certified that error appears in the above-identified patent and that said Letters Patent is hereby corrected as shown below:

Column 16,
Line 58, after the words "according to", delete "claim 1" and insert -- claim 10 -- therefor; and
Line 62, after the words "expression in," delete "targets" and insert therefor -- target --.

Signed and Sealed this

Sixteenth Day of November, 2004

JON W. DUDAS
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:1:

GTGGTCCAGG CTCTAGTTTT                20

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

GGGCACATAG GTTATTTGGG AG          22

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

TGTTGCTTCT ATGCGGACCA          20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

CCGCGCTTAT TAGCCTGTTA          20